United States Patent
Komata et al.

(10) Patent No.: US 7,385,079 B2
(45) Date of Patent: Jun. 10, 2008

(54) PROCESS FOR PRODUCING α-SUBSTITUTED ACRYLIC NORBORNANYYL COMPOUNDS

(75) Inventors: Takeo Komata, Kawagoe (JP); Shinya Akiba, Kawagoe (JP); Satoru Miyazawa, Kawagoe (JP); Takahisa Tada, Kawagoe (JP); Yusuke Kuramoto, Kawagoe (JP); Seiji Murata, Kawagoe (JP)

(73) Assignee: Central Glass Company, Limited, Ube-shi (JP)

(*) Notice: Subject to any disclaimer, the term of this patent is extended or adjusted under 35 U.S.C. 154(b) by 387 days.

(21) Appl. No.: 10/995,335

(22) Filed: Nov. 24, 2004

(65) Prior Publication Data
US 2005/0131248 A1 Jun. 16, 2005

(30) Foreign Application Priority Data
Nov. 26, 2003 (JP) .............................. 2003-396040

(51) Int. Cl.
*C07C 69/52* (2006.01)
(52) U.S. Cl. .................................................. 560/220
(58) Field of Classification Search ................. 560/220
See application file for complete search history.

(56) References Cited
FOREIGN PATENT DOCUMENTS
JP 2003-040840 2/2003
JP 2004-175740 6/2004

OTHER PUBLICATIONS
T. Chiba et al., "157 nm Resist Materials: A Progress Report" J. Photopolym. Sci. Technol. vol. 13, No. 4, 2000, p. 657.

*Primary Examiner*—Taylor Victor Oh
(74) *Attorney, Agent, or Firm*—Crowell & Moring LLP

(57) ABSTRACT

A process for producing an α-substituted acrylic norbornanyl compound represented by the formula [3] includes reacting an α-substituted acrylic acid anhydride represented by the formula [1] with a substituted norbornanyl alcohol represented by the formula [2].

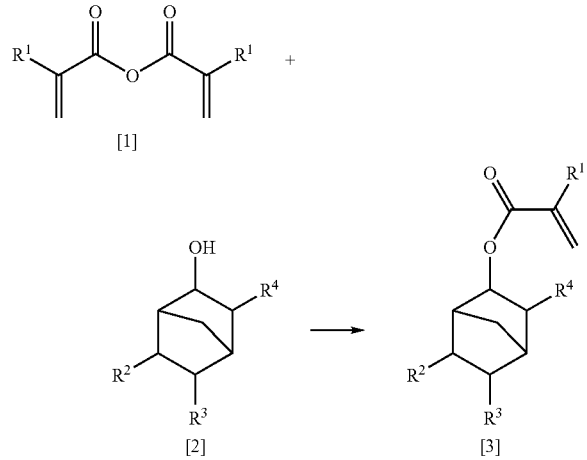

wherein $R^1$ represents a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, and wherein one of $R^2$, $R^3$ and $R^4$ is a $CF_3C(CF_3)(OH)CH_2$— group, and each of the other two of $R^2$, $R^3$ and $R^4$ is a hydrogen.

19 Claims, No Drawings

PROCESS FOR PRODUCING α-SUBSTITUTED ACRYLIC NORBORNANYYL COMPOUNDS

BACKGROUND OF THE INVENTION

The present invention relates to a process of producing α-substituted acrylic norbornanyl compounds, which are useful as monomers adapted to the next generation photoresists.

It is known that α-substituted acrylic norbornanyl compounds have bright prospects as monomers for the next generation resist materials and that such resists containing the monomers as their constituent element are superior in light transmission and surface adhesion (see U.S. Pat. No. 6,784,312 corresponding to Japanese Patent Laid-open Publication 2003-040840).

It is possible to synthesize an α-substituted acrylic norbornanyl compound by a dehydration and condensation reaction of an α-substituted acrylic acid with a norbornanyl alcohol (see U.S. Pat. No. 6,784,312) or by a reaction of α-substituted acrylic chloride with a norbornanyl alcohol (see U.S. Pat. No. 6,784,312).

Japanese Patent Laid-open Publication 2004-175740 (Application No. 2002-345084) discloses a process for producing an α-substituted acrylic norbornanyl compound by reacting an α-substituted acrylic acid with a substituted norbornene.

SUMMARY OF THE INVENTION

It is an object of the present invention to provide a process for producing an α-substituted acrylic norbornanyl compound, which is suitable for an industrial scale production.

According to the present invention, there is provided a process for producing an α-substituted acrylic norbornanyl compound represented by the formula [3],

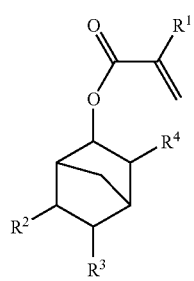

wherein $R^1$ represents a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, and wherein one of $R^2$, $R^3$ and $R^4$ is a $CF_3C(CF_3)(OH)CH_2$— group, and each of the other two of $R^2$, $R^3$ and $R^4$ is a hydrogen.

This process comprises reacting an α-substituted acrylic acid anhydride represented by the formula [1],

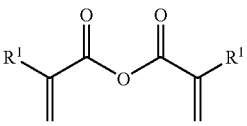

wherein $R^1$ is defined as above, with a substituted norbornanyl alcohol represented by the formula [2],

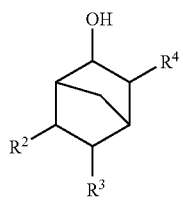

wherein $R^2$, $R^3$ and $R^4$ are defined as above.

DETAILED DESCRIPTION

The present inventors have unexpectedly found that an α-substituted acrylic norbornanyl compound represented by the formula [3] can be produced with a remarkably higher selectivity and a remarkably higher yield, as compared with the process of Japanese Patent Laid-open Publication 2004-175740, by one-step reaction in which an α-substituted acrylic acid anhydride represented by the formula [1] is reacted with a substituted norbornanyl alcohol represented by the formula [2], as shown by the following reaction scheme.

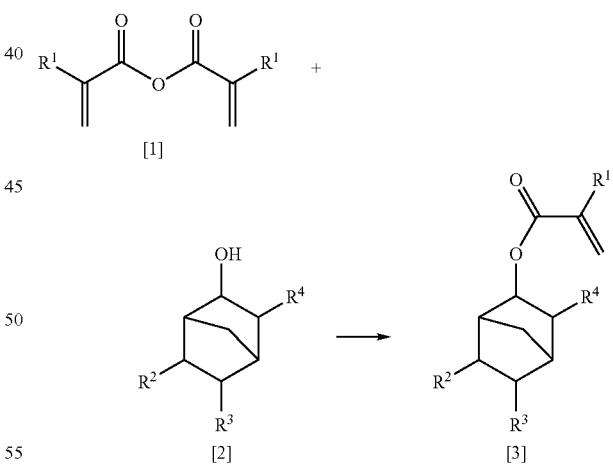

Furthermore, we have unexpectedly found that it is possible to obtain the target α-substituted acrylic norbornanyl compound of high purity by distilling the reaction liquid itself after the reaction. According to the process of the present invention, it becomes possible to minimize waste problem and post treatment load. Thus, this process is particularly suitable for industrially producing the target α-substituted acrylic norbornanyl compound.

The process of the present invention can be conducted by using a batch-wise reaction device. Reaction conditions of the process are exemplarily described in detail in the following. Certain modifications of the reaction conditions can be made by a person skilled in the art in respective reaction devices.

The α-substituted acrylic acid anhydride represented by the formula [1] wherein $R^1$ is defined as above can be synthesized by a conventional process. If $R^1$ is a hydrogen atom, methyl group or the like, the α-substituted acrylic acid anhydride is easily available as a reagent.

It is known that the substituted norbornanyl alcohol represented by the formula [2] can be synthesized by a hydroboration of a corresponding substituted norbornene (see U.S. Pat. No. 6,784,312). In this synthesis, the positional selectivity of the alcohol addition to the norbornene is generally low, Therefore, the resulting substituted norbornanyl alcohol is in the form of a mixture of three isomers having $CF_3C(CF_3)(OH)CH_2$— groups at the positions of $R^2$, $R^3$ and $R^4$ of the formula [2], respectively. This isomeric mixture can be used in the reaction of the present invention. Alternatively, the isomeric mixture may be purified, and the resulting single isomer can be used in the reaction of the present invention. It is known that the substituted norbornene can be synthesized by a Diels-Alder reaction in which a corresponding olefin is reacted with a cyclopentadiene in the presence or absence of a Lewis acid catalyst. It is disclosed in J. Photopolym. Sci. Technol., Vol. 13, No. 4, 2000, p. 657 that a compound with a $CF_3C(CF_3)(OH)CH_2$— group can be obtained with a yield of 33% by reacting 1,1,1-trifluoro-2-(trifluoromethyl)pent-4-ene-2-ol with a cyclopentadiene. It is disclosed in this publication that 1,1,1-trifluoro-2-(trifluoromethyl)pent-4-ene-2-ol used as a reagent in this reaction can be synthesized, for example, by reacting an allyl Grignard reagent with hexafluoroacetone.

The amount of the α-substituted acrylic acid anhydride used in the present invention may be the same as, or slightly in excess of, that of the substituted norbornanyl alcohol. It may be 0.5 to 3.0 moles, preferably 0.7 to 2.0 moles, more preferably 1.0 to 1.6 moles, per mol of the substituted norbornanyl alcohol. If it is less than 0.5 moles per mol of the substituted norbornanyl alcohol, selectivity of the reaction and yield of the target product may become too low. If it exceeds 3.0 moles per that, the amount of the α-substituted acrylic acid anhydride that is not involved with the reaction may become too much. This is not preferable from the economical viewpoint due to its disposal load.

In the present invention, it is possible to add an additive for accelerating the reaction. The reaction may proceed with a sufficient reaction rate at a lower temperature by adding an additive. This can improve selectivity of the target product. This additive may be an organic sulfonic acid (e.g., methanesulfonic acid, ethanesulfonic acid, p-toluenesulfonic acid, benzenesulfonic acid, trifluoromethanesulfonic acid, and pentafluoroethanesulfonic acid) or Lewis acid (e.g., $BF_3$, $BCl_3$, and anhydrous hydrogen fluoride). Of these, organic sulfonic acid is preferable.

In the present invention, however, it is possible obtain relatively high reaction rate and high reaction selectivity, even if the additive is not added. Thus, it is optional to conduct the reaction without using the additive depending on the target reaction rate and the target reaction selectivity. In the case of not using the additive, it becomes an advantage that the removal of the additive can be omitted.

In the case of adding the additive, its amount may be 0.01 to 1.5 moles, preferably 0.02 to 1.2 moles, more preferably 0.05 to 1.0 mole, per mol of the substituted norbornanyl alcohol. If it is less than 0.01 moles, the advantageous effect of adding the additive may become insufficient. If it exceeds 1.5 moles, the amount of the additive that is not involved in the reaction may become too much. With this, the removal of the additive after the reaction may take too much effort in some cases.

In the case of not using the additive, the reaction temperature may be 20 to 200° C., preferably 50 to 180° C., more preferably 80 to 160° C. If it is lower than 20° C., the reaction rate may become too low. If it is higher than 200° C., the α-substituted acrylic acid anhydride (as the raw material) or α-substituted acrylic norbornanyl compound (as the product) may polymerize. In the case of adding the additive, the reaction temperature may be −50 to +60° C., preferably −30 to +40° C., more preferably −20 to +30° C. If it is lower than −50° C., the reaction rate may become too low. If it is higher than +60° C., the production of cyclized compounds may become too much.

Although the reaction may proceed without using solvent, it is preferable to use a solvent in view of achieving reaction homogeneity and improving operability after the reaction. Examples of the solvent include aromatic compounds (e.g., benzene, toluene, xylene, and mesitylene), ethers (e.g., diethyl ether, methyl-tert-butyl ether, diisopropyl ether, and tetrahydrofuran), and halogen-containing compounds (e.g., methylene chloride, chloroform, and carbon tetrachloride). It is optional to use a single solvent or a mixture of solvents.

In the case of using a solvent, its amount may be 0.2 to 50 g, preferably 0.5 to 20 g, more preferably 1.0 to 10 g, per 1 g of the substituted norbornanyl alcohol. If it exceeds 50 g, it may be economically not preferable from the viewpoint of productivity.

It is optional to conduct the reaction in the presence of a polymerization inhibitor for the purpose of suppressing polymerization of the α-substituted acrylic acid anhydride or α-substituted acrylic norbornanyl compound. The polymerization inhibitor may be at least one compound selected from 2,5-di-t-butylhydroquinone, 1,2,4-trihydroxybenzene, 2,5-bistetramethylbutylhydroquinone, leucoquinizarin, phenothiazine, tetraethylthiuram, disulfide, 1,1-diphenyl-2-picrylhydrazyl, and 1,1-diphenyl-2-picrylhydrazine Further examples expressed in trade name include NONFLEX F, NONFLEX H, NONFLEX DCD, NONFLEX MBP, and OZONONE 35 of SEIKO CHEMICAL Co., Ltd located in Japan, and Q-1300 and Q-1301 of Wako Pure Chemical Industries, Ltd. located in Japan.

The above examples of the polymerization inhibitor are commercial products and therefore easily available. In the case of using a polymerization inhibitor in the reaction, its amount may be 0.000005 to 0.1 moles, preferably 0.00001 to 0.05 moles, more preferably 0.0001 to 0.03 moles, per mol of the substituted norbornanyl alcohol. Even if it exceeds 0.1 moles per that, the effect of suppressing the polymerization may not improve further. Thus, this may be economically not preferable.

The reaction vessel may be made of a resin material (e.g., ethylene tetrafluoride resin, chlorotrifluoroethylene resin, vinylidene fluoride resin, and PFA resin). It may be one lined with glass or the like. Furthermore, it may be a glass vessel or stainless steel vessel.

For example, it is possible to conduct the reaction by charging a reaction vessel that is proof against the reaction conditions with a solvent, the substituted norbornanyl alcohol, the α-substituted acrylic acid anhydride, and a polymerization inhibitor, followed by heating from outside with stirring to make the reaction proceed. It is preferable to monitor the reaction by sampling or the like to determine the reaction end point, followed by cooling the reaction liquid.

It is possible to use a conventional method for purifying the α-substituted acrylic norbornanyl compound represented by the formula [3]. For example, the reaction liquid is washed with water, followed by distilling the solvent off. The resulting crude organic matter can be purified by column chromatography, distillation or the like to obtain the target α-substituted acrylic norbornanyl compound of high purity. In the present invention, however, the target α-substituted acrylic norbornanyl compound of high purity can be obtained by directly distilling the reaction liquid itself.

In the present invention, it is possible to use an isomeric mixture (a mixture of three isomers) of the substituted norbornanyl alcohol. In this case, the target α-substituted acrylic norbornanyl compound is in the form of a mixture of corresponding three positional isomers, that is, the first isomer [3a] ($R^2$: a $CF_3C(CF_3)(OH)CH_2$— group, $R^3$: H, and $R^4$: H), the second isomer [3b] ($R^2$: H, $R^3$: a $CF_3C(CF_3)(OH)CH_2$— group, and $R^4$: H), and the third isomer [3c] ($R^2$: H, $R^3$: H, and $R^4$: a $CF_3C(CF_3)(OH)CH_2$— group). In view of exo- and endo-conformations of a norbornene, the target compound is usually in the form of a mixture of 12 kinds of isomers. It is possible to isolate a single isomer as the final product by column chromatography or the like. Alternatively, the isomeric mixture can be used as a monomer without conducting the isolation, for preparing photoresists.

The following nonlimiting examples are illustrative of the present invention. Herein, the percent (%) of the compositional analysis value refers to area 1% of an organic component (other than the solvent component) obtained by gas chromatography of a sampled reaction mixture.

EXAMPLE 1

A 500 mL three-necked flask equipped at its upper part with a reflux condenser was charged with 250 mL of toluene, 39.0 g (0.253 moles) of methacrylic acid anhydride, and 50.0 g (0.171 moles) of a mixture of first, second and third isomers 3-[3,3,3-trifluoro-2-hydroxy-2-(trifluoromethyl)propyl]-norbornane-2-ol, 5-[3,3,3-trifluoro-2-hydroxy-2-(trifluoromethyl)propyl]-norbornane-2-ol and 6-[3,3,3-trifluoro-2-hydroxy-2-(trifluoromethyl)propyl]-norbornane-2-ol, and 0.15 g of NONFLEX MBP, followed by heating at 115° C.

8 hr later, the composition of the reaction mixture was analyzed by gas chromatography. With this, it was found that the reaction mixture (except toluene, the remaining methacrylic acid anhydride, and methacrylic acid produced as a by-product) contained 90.8% of the total of a mixture of three isomers of the target norbornanyl methacrylate, 4.2% of impurities containing 5,5-bis(trifluoromethyl)-4-oxatricyclo[5.2.1.0$^{3,8}$]decane (hereinafter referred to as "the cyclized compound"), and 5.0% of the total of the first, second and third isomers as the raw materials. In fact, the cyclized compound is a compound formed by an occurrence where the norbornanyl methacrylate released methacrylic acid and then cyclized within the molecule. The impurities containing the cyclized compound refers to a mixture of (a) several unidentified compounds containing a skeleton of 5,5-bis(trifluoromethyl)-4-oxatricyclo[5.2.1.0$^{8,8}$]decane and (b) other unidentified compounds.

After cooling the reaction liquid, it was washed with 200 mL of water. The resulting solution was dried with 20 g of magnesium sulfate, followed by removal of magnesium sulfate by filtration and then distilling the solvent off, thereby obtaining 79 g of a crude organic matter. This crude organic matter was subjected to a distillation under reduced pressure (0.1 Torr=13 Pa), and a distillate boiling at 110° C. to 135° C. was collected, thereby obtaining 35.0 g of an isomeric mixture of norbornanyl methacrylate. This product was found by gas chromatography to contain 95.5% (the total selectivity) of a mixture of the target three isomers 3-[3,3,3-trifluoro-2-hydroxy-2-(trifluoromethyl)propyl]-norbornane-2-yl 2-methacrylate, 5-[3,3,3-trifluoro-2-hydroxy-2-(trifluoromethyl)propyl]-norbornane-2-yl 2-methacrylate and 6-[3,3,3-trifluoro-2-hydroxy-2-(trifluoromethyl)propyl]-norbornane-2-yl 2-methacrylate, 0.4% of the cyclized compound, 2.2% of the total of the first, second and third isomers as the raw materials, and 1.9% of others. The yield was 54%

EXAMPLE 2

A 500 mL three-necked flask equipped at its upper part with a reflux condenser was charged with 250 mL of xylene, 36.9 g (0.239 moles) of methacrylic acid anhydride, and 50.0 g (0.171 moles) of a mixture of the first, second and third isomers defined as in Example 1, and 0.15 g of NONFLEX MBP, followed by heating at 130° C.

3 hr later, the composition of the reaction mixture was analyzed by gas chromatography. With this, it was found that the reaction mixture (except xylene, the remaining methacrylic acid anhydride, and methacrylic acid produced as a by-product) contained 92.3% of the total of a mixture of three isomers of the target norbornanyl methacrylate, 3.7% of the cyclized compound-containing impurities defined as in Example 1, and 4.0% of the total of the first, second and third isomers as the raw materials.

After cooling the reaction liquid, the solvent was distilled off, thereby obtaining 78 g of a crude organic matter. This crude organic matter was subjected to a distillation under reduced pressure (0.1 Torr=13 Pa), and a distillate boiling at 110° C. to 135° C. was collected, thereby obtaining 36.0 g of an isomeric mixture of norbornanyl methacrylate. This product was found by gas chromatography to contain 96.5% (the total selectivity) of a mixture of the target three isomers defined as in Example 1, 0.2% of the cyclized compound, 1.9% of the total of the first, second and third isomers as the raw materials, and 1.4% of others. The yield was 56%.

EXAMPLE 3

A 100 mL three-necked flask equipped at its upper part with a reflux condenser was charged with 63 mL of toluene, 6.5 g (0.0515 moles) of acrylic acid anhydride, and 12.0 g (0.411 moles) of a mixture of the first, second and third isomers defined as in Example 1, and 0.06 g of NONFLEX MBP, followed by heating at 115° C.

3 hr later, the composition of the reaction mixture was analyzed by gas chromatography. With this, it was found that the reaction mixture (except toluene, the remaining acrylic acid anhydride, and acrylic acid produced as a by-product) contained 92.1% of the total of a mixture of three isomers of the target norbornanyl acrylate, 0.9% of the cyclized compound, and 7.0% of the total of the first, second and third isomers as the raw materials. After cooling the reaction liquid, it was washed with 70 ml of water.

The resulting solution was dried with 5 g of magnesium sulfate, followed by removal of magnesium sulfate by filtration and then distilling the solvent off, thereby obtaining 16.0 g of a crude organic matter. This crude organic matter was subjected to a distillation under reduced pressure (7 Torr=933 Pa), and a distillate boiling at 142° C. to 150° C. was collected, thereby obtaining 8.3 g of an isomeric mixture of norbornanyl acrylate. This product was found by gas chromatography to contain 96.5% (the total selectivity) of a mixture of the target three isomers 3-[3,3,3-trifluoro-2-hydroxy-2-(trifluoromethyl)propyl]-norbornane-2-yl acrylate, 5-[3,3,3-trifluoro-2-hydroxy-2-(trifluoromethyl)propyl]-norbornane-2-yl acrylate and 6-[3,3,3-trifluoro-2-hydroxy-2-(trifluoromethyl)propyl]-norbornane-2-yl acrylate, 0.2% of a cyclized compound, 0.5% of the total of the first, second and third isomers as the raw materials, and 2.8% of others. The yield was 56%. In fact, this cyclized compound is a compound formed by an occurrence where the norbornanyl acrylate released acrylic acid and then cyclized within the molecule.

EXAMPLE 4

A 500 mL three-necked flask equipped at its upper part with a reflux condenser was charged with 250 mL of toluene, 27.5 g (0.178 moles) of methacrylic acid anhydride, and 50.0 g (0.171 moles) of a mixture of the first, second and third isomers defined as in Example 1, 1.64 g (0.017 moles) of methanesulfonic acid, and 0.15 g of NONFLEX MBP, followed by conducting the reaction at 20° C. to 25° C. 8 hr later, the composition of the reaction mixture was analyzed by gas chromatography. With this, it was found that the reaction mixture (except toluene, the remaining methacrylic acid anhydride, and methacrylic acid produced as a by-product) contained 85.1% of the total of a mixture of three isomers of the target norbornanyl methacrylate, 9.9% of the cyclized compound-containing impurities defined as in Example 1, and 5.0% of the total of the first, second and third isomers as the raw materials.

The reaction liquid was washed with 200 mL of water. The resulting solution was dried with 20 g of magnesium sulfate, followed by removal of magnesium sulfate by filtration and then distilling the solvent off, thereby obtaining 72 g of a crude organic matter. This crude organic matter was subjected to a distillation under reduced pressure (0.1 Torr=13 Pa), and a distillate boiling at 110° C. to 135° C. was collected, thereby obtaining 33.0 g of an isomeric mixture of norbornanyl methacrylate. This product was found by gas chromatography to contain 95.5% (the total selectivity) of a mixture of the target three isomers defined as in Example 1, 0.2% of the cyclized compound, 2.0% of the total of the first, second and third isomers as the raw materials, and 2.3% of others. The yield was 51%.

COMPARATIVE EXAMPLE 1

A 20 mL three-necked flask (equipped with a thermometer, a water quantitative receiver, and a reflux condenser) was charged with a stirrer magnet coated with ethylene tetrafluoride resin, 15 mL of toluene, 3.58 g (0.0188 moles) of p-toluenesulfonic acid monohydrate, 1.62 g (0.0188 moles) of methacrylic acid, and 5.0 g (0.0171 moles) of a mixture of the first, second and third isomers defined as in Example 1, and 0.015 g of NONFLEX MBP. The water quantitative receiver was also charged with 20 mL of toluene. The reaction mixture was heated with an oil bath of 140° C. under reflux. 1 hr later, the composition of the reaction mixture was analyzed by gas chromatography. With this, it was found that the reaction mixture contained 2.25% of the total of a mixture of three isomers of the target norbornanyl methacrylate, 95.06% of the cyclized compound, and 2.69% of other impurities.

COMPARATIVE EXAMPLE 2

A 20 mL two-necked flask equipped at its upper par with a reflux condenser was charged with 10 mL of toluene, 0.14 g (0.00074 moles) of p-toluenesulfonic acid monohydrate, 1.05 g (0.0146 moles) of acrylic acid, and 1.0 g (0.00365 moles) of 5-[3,3,3-trifluoro-2-hydroxy-2-(trifluoromethyl)propyl]-norbornene, followed by heating with an oil bath of 140° C. under reflux. 7 hr later, the composition of the reaction mixture was analyzed by gas chromatography. With this, it was found that the reaction mixture contained 48.1% of the total of a mixture of three isomers of the target norbornanyl acrylate, 35% of the cyclized compound, and 2.5% of 5-[3,3,3-trifluoro-2-hydroxy-2-(trifluoromethyl) propyl]- norbornene.

What is claimed is:

1. A process for producing an α-substituted acrylic norbornanyl compound represented by the formula [3],

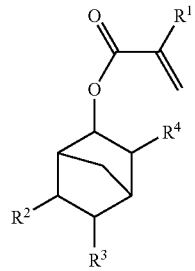

[3]

wherein $R^1$ represents a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, and wherein one of $R^2$, $R^3$ and $R^4$ is a $CF_3C(CF_3)(OH)CH_2$—group, and each of the other two of $R^2$, $R^3$ and $R^4$ is a hydrogen, the process comprising reacting an α-substituted acrylic acid anhydride represented by the formula [1],

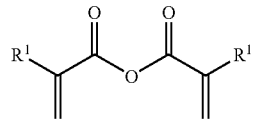

[1]

wherein $R^1$ is defined as above, with a substituted norbornanyl alcohol represented by the formula [2],

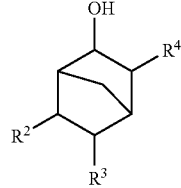

[2]

wherein $R^2$, $R^3$ and $R^4$ are defined as above; and
wherein
the reaction is conducted in the presence of at least one additive that is an organic sulfonic acid or Lewis acid at a temperature of −50° C. to +60° C.,
or
the reaction is conducted in the absence of any organic sulfonic acid or Lewis acid at a temperature of +20° C. to +200° C.

2. A process according to claim 1, wherein $R^1$ represents a hydrogen atom, methyl group, ethyl group, n-propyl group, isopropyl group, n-butyl group, sec-butyl group, or tert-butyl group.

3. A process according to claim 1, wherein $R^1$ represents a hydrogen atom or methyl group.

4. A process according to claim 1, wherein the α-substituted acrylic acid anhydride is in an amount of 0.5 to 3.0 moles per mol of the substituted norbornanyl alcohol.

5. A process according to claim 1, wherein the α-substituted acrylic acid anhydride is in an amount of 0.7 to 2.0 moles per mol of the substituted norbornanyl alcohol.

6. A process according to claim 1, wherein the α-substituted acrylic acid anhydride is in an amount of 1.0 to 1.6 moles per mol of the substituted norbornanyl alcohol.

7. A process according to claim 1, wherein the reaction is conducted in the presence of an α-substituted acrylic acid anhydride and in the absence of any acid other than said α-substituted acrylic acid anhydride.

8. A process according to claim 1, wherein the reaction is conducted in the presence of at least one additive that is an organic sulfonic acid or Lewis acid.

9. A process according to claim 8, wherein the at least one additive is an organic sulfonic acid.

10. A process according to claim 9, wherein the organic sulfonic acid is selected from the group consisting of methanesulfonic acid, ethanesulfonic acid, p-toluenesulfonic acid, benzenesulfonic acid, trifluoromethanesulfonic acid, and pentafluoroethanesulfonic acid.

11. A process according to claim 8, wherein the at least one additive is a Lewis acid that is selected from the group consisting of $BF_3$, $BCl_3$, and anhydrous hydrogen fluoride.

12. A process according to claim 8, wherein the at least one additive is in an amount of 0.01 to 1.5 moles per mol of the substituted norbornanyl alcohol.

13. A process according to claim 8, wherein the at least one additive is in an amount of 0.02 to 1.2 moles per mol of the substituted norbornanyl alcohol.

14. A process according to claim 8, wherein the at least one additive is in an amount of 0.05 to 1.0 mole per mol of the substituted norbornanyl alcohol.

15. A process according to claim 1, wherein the reaction is conducted at a temperature of +20° C. to +200° C. in the absence of any additive that is an organic sulfonic acid or Lewis acid.

16. A process according to claim 1, wherein the reaction is conducted in the presence of a polymerization inhibitor.

17. A process for producing an α-substituted acrylic norbornanyl compound represented by the formula [3],

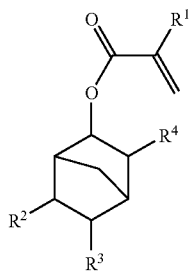

[3]

wherein $R^1$ represents a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, and wherein one of $R^2$, $R^3$ and $R^4$ is a $CF_3C(CF_3(OH)CH_2$— group, and each of the other two of $R^2$, $R^3$ and $R^4$ is a hydrogen, the process comprising reacting 0.5-3.0 parts by mole of an α-substituted acrylic acid anhydride represented by the formula [1],

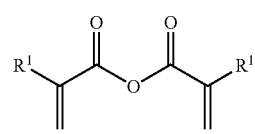

[1]

wherein $R^1$ is defined as above, with one part by mole of a substituted norbornanyl alcohol represented by the formula [2],

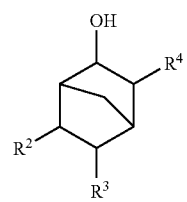

[2]

wherein $R^2$, $R^3$ and $R^4$ are defined as above, in the presence of 0.01-1.5 parts by mole of an additive that is at least one compound selected from organic sulfonic acids and Lewis acids, and in the presence of a polymerization inhibitor; and wherein the reaction is conducted at a temperature of −50° C. to +60° C.

18. A process according to claim 17, wherein the additive is at least one compound selected from organic sulfonic acids.

19. A process according to claim 18, wherein the organic sulfonic acids are methanesulfonic acid, ethanesulfonic acid, p-toluenesulfonic acid, benzenesulfonic acid, and trifluoromethanesulfonic acid.

* * * * *